US011345954B2

(12) United States Patent
Martineau et al.

(10) Patent No.: US 11,345,954 B2
(45) Date of Patent: May 31, 2022

(54) METHODS FOR DIGITAL READOUT QUANTIFICATION OF NUCLEIC ACIDS

(71) Applicant: ARIZONA BOARD OF REGENTS ON BEHALF OF ARIZONA STATE UNIVERSITY, Scottsdale, AZ (US)

(72) Inventors: Rhett Martineau, Gilbert, AZ (US); Deirdre Meldrum, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 293 days.

(21) Appl. No.: 16/323,393

(22) PCT Filed: Aug. 7, 2017

(86) PCT No.: PCT/US2017/045800
§ 371 (c)(1),
(2) Date: Feb. 5, 2019

(87) PCT Pub. No.: WO2018/027236
PCT Pub. Date: Feb. 8, 2018

(65) Prior Publication Data
US 2020/0385794 A1 Dec. 10, 2020

Related U.S. Application Data

(60) Provisional application No. 62/371,555, filed on Aug. 5, 2016.

(51) Int. Cl.
*C12Q 1/6851* (2018.01)
*C12Q 1/6853* (2018.01)

(52) U.S. Cl.
CPC ......... *C12Q 1/6851* (2013.01); *C12Q 1/6853* (2013.01); *C12Q 2525/307* (2013.01); *C12Q 2563/107* (2013.01); *C12Q 2565/101* (2013.01); *C12Q 2565/625* (2013.01)

(58) Field of Classification Search
CPC ...... C12Q 1/6851; C12Q 1/6853; C12Q 1/68; C12Q 1/686; C12Q 1/6844; C12P 19/34
See application file for complete search history.

(56) References Cited

U.S. PATENT DOCUMENTS

| | | |
|---|---|---|
| 8,748,192 B2 | 6/2014 | Tian et al. |
| 9,359,638 B2 | 6/2016 | Takahashi et al. |
| 9,410,970 B2 | 8/2016 | Tian et al. |
| 9,597,026 B2 | 3/2017 | Meldrum et al. |
| 10,022,718 B2 | 7/2018 | Martineau et al. |
| 10,156,573 B2 | 12/2018 | Tian et al. |
| 10,162,162 B2 | 12/2018 | Wang et al. |
| 10,221,443 B2 | 3/2019 | Meldrum et al. |
| 10,260,090 B2 | 4/2019 | Martineau et al. |
| 10,391,485 B2 | 8/2019 | Meldrum et al. |
| 10,471,426 B2 | 11/2019 | Martineau et al. |
| 10,590,155 B2 | 3/2020 | Kong et al. |
| 2008/0057513 A1 | 3/2008 | Farrell |
| 2012/0164652 A1 | 6/2012 | Clemens et al. |
| 2012/0231533 A1 | 9/2012 | Holl et al. |
| 2012/0301913 A1 | 11/2012 | Youngbull et al. |
| 2013/0171643 A1 | 7/2013 | Kubota et al. |
| 2015/0253333 A1 | 9/2015 | Tian et al. |
| 2016/0076083 A1 | 3/2016 | Ellington et al. |
| 2016/0202247 A1 | 7/2016 | Tian et al. |
| 2016/0215254 A1 | 7/2016 | Meldrum et al. |
| 2018/0264468 A1 | 9/2018 | Anderson et al. |
| 2018/0334700 A1 | 11/2018 | Messner et al. |
| 2019/0126275 A1 | 5/2019 | Kelbauskas et al. |
| 2019/0177784 A1 | 6/2019 | Martineau et al. |

(Continued)

FOREIGN PATENT DOCUMENTS

| | | |
|---|---|---|
| WO | 2010062654 A2 | 6/2010 |
| WO | WO 2010/062654 | 6/2010 |

(Continued)

OTHER PUBLICATIONS

Martineau et al, Improved Performance of Loop-Mediated Isothermal Amplification Assays via Swarm Priming, 2017, Anal. Chem., 89, 625-632. (Year: 2017).*
Martineau et al. Improved Performance of Loop-Mediated Isothermal Amplification, Analytical Chemistry, 2016.
Martineau et al. Improved Performance of Loop-Mediated Isothermal Amplification Assays via Swarm Priming, Analytical chemistry, Jan. 2017.
Ball et al. Quenching of Unincorporated Amplification Signal Reporters in Reverse-Transcription Loop-MediatedIsothermal Amplification Enabling Bright, Single-Step, Closed-Tube, and Multiplexed Detection of RNA Viruses, Analytical chemistry, 2016.
Wang, et al. Rapid and Sensitive Isothermal Detection of Nucleic-acid Sequence by Multiple Cross Displacement Amplification, Scientific reports, Jul. 2015.

(Continued)

*Primary Examiner* — Narayan K Bhat
(74) *Attorney, Agent, or Firm* — Casimir Jones, S.C.; Peter J. Schlueter

(57) ABSTRACT

The invention provides methods for detecting specific nucleic acids using a loop-mediated isothermal amplification (LAMP) reaction and providing a digital readout of the results. One method teaches separating target specificity from indicator detection in a two-stage multiple-threshold array (MTA). During the first stage amplicons incorporating both target sequence and an indicator sequence are synthesized. During the second stage of the reaction, the indicator sequence is targeted and amplified to produce visual results that may be digitalized. Another method teaches a competitive MTA, in which a reference sequence is used to compete against target sequence during amplification producing threshold responses, thus enabling digital readout. Using either method, quantitation is achieved without the need for continuous monitoring of the reaction and the end-point readout is amenable to visual inspection. Methods of the invention are especially useful in circumstances where there is lower or intermittent power supply.

20 Claims, 16 Drawing Sheets
Specification includes a Sequence Listing.

(56) References Cited

U.S. PATENT DOCUMENTS

| | | |
|---|---|---|
| 2019/0346361 A1 | 11/2019 | Meldrum et al. |
| 2019/0360984 A1 | 11/2019 | Zhang et al. |
| 2020/0047182 A1 | 2/2020 | Meldrum et al. |
| 2020/0049694 A1 | 2/2020 | Anderson et al. |
| 2020/0058140 A1 | 2/2020 | Meldrum et al. |
| 2020/0063197 A1 | 2/2020 | Meldrum et al. |
| 2020/0406253 A1 | 12/2020 | Meldrum et al. |

FOREIGN PATENT DOCUMENTS

| | | |
|---|---|---|
| WO | 2015048009 A1 | 4/2015 |
| WO | WO 2015/048009 | 4/2015 |
| WO | WO2015/160536 | 10/2015 |
| WO | WO 2015/160536 | 10/2015 |
| WO | WO 2016/073255 | 5/2016 |
| WO | WO2016/073255 | 5/2016 |
| WO | 2017049122 A1 | 3/2017 |
| WO | WO 2017/049122 | 3/2017 |
| WO | 2017062807 A1 | 4/2017 |
| WO | WO 2017/062807 | 4/2017 |
| WO | 2017083817 A1 | 5/2017 |
| WO | 2017087473 A1 | 5/2017 |
| WO | WO 2017/083817 | 5/2017 |
| WO | WO 2017/087473 | 5/2017 |
| WO | 2017151978 A1 | 9/2017 |
| WO | WO 2017/151978 | 9/2017 |
| WO | 2017184998 A1 | 10/2017 |
| WO | WO 2017/184998 | 10/2017 |
| WO | 2018013948 A1 | 1/2018 |
| WO | WO 2018/013948 | 1/2018 |
| WO | 2018027238 A1 | 2/2018 |
| WO | WO 2018/027238 | 2/2018 |
| WO | 2018136794 A1 | 7/2018 |
| WO | WO 2018/136794 | 7/2018 |
| WO | 2018157064 A1 | 8/2018 |
| WO | WO 2018/157064 | 8/2018 |
| WO | 2018160998 A1 | 9/2018 |
| WO | WO 2018/160998 | 9/2018 |
| WO | 2018213269 A1 | 11/2018 |
| WO | WO 2018/213269 | 11/2018 |

OTHER PUBLICATIONS

Notification of Transmittal of International Search Report and the Written Opinion of the International Searching Authority, or the Declaration PCT/US2017/045800.

Ihira et al. "Rapid Diagnosis of Human Herpesvirus 6 Infection by a Novel DNA Amplification Method, Loop-Mediated Isothermal Amplification." Journal of Clinical Microbiology.

U.S. Appl. No. 16/479,729, filed Jul. 22, 2019, Meldrum et al.

Fujitsu Limited, "PrimerExplorer" [online], Fujitsu Limited, retrieved on Dec. 30, 2020 from archive.org, as it appeared on Mar. 20, 2016, retrieved from the internet: <https://web.archive.org/web/20160320160049/http://primerexplorer.jp/e/intro/index.html>.

Ball et al., Quenching of Unincorporated Amplification Signal Reporters in Reverse-Transcription Loop-Mediated Isothermal Amplification Enabling Bright, Single-Step, Closed-Tube, and Multiplexed Detection of RNA Viruses. Anal Chem. Apr. 5, 2016;88(7):3562-8.

Fujitsu Limited "PrimeExplorer" [online], Fujitsu Limited, retrieved on Dec. 30, 2020 from archive.org as it appeared on Mar. 20, 2016. retrieved from the internet: <https://webarchive.org/web/20160320160049/http://primerexplorer.jp/e/intro/index.html> 1 page.

Ihira et al., Rapid Diagnosis of Human Herpesvirus 6 Infection by a Novel DNA Amplification Method, Loop-Mediated Isothermal Amplification. J Clin Microbiol. Jan. 2004;42(1):140-5.

Martineau et al. Improved Performance of Loop-Mediated Isothermal Amplification Assays via Swarm Priming. Anal Chem. Jan. 3, 2017;89(1):625-632.

Wang et al., Rapid and Sensitive Isothermal Detection of Nucleic-acid Sequence by Multiple Cross Displacement Amplification. Sci Rep. Jul. 8, 2015;5:11902. 16 pages.

International Search Report and Written Opinion for PCT/US2017/045800. Dated Oct. 23, 2017. 13 pages.

\* cited by examiner

FIG 3
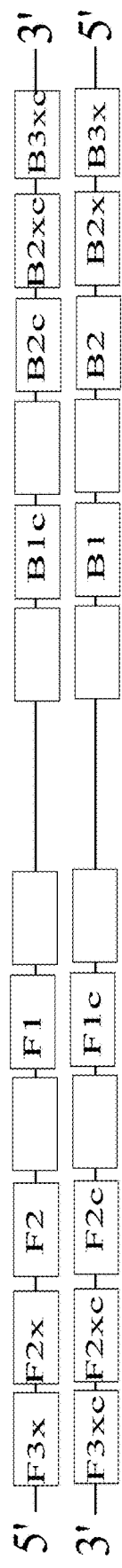
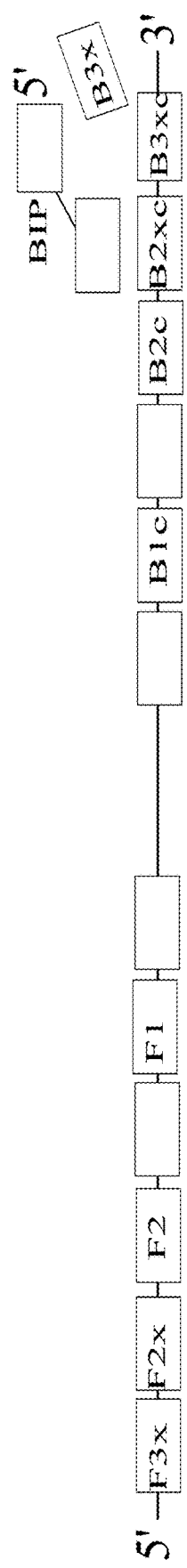
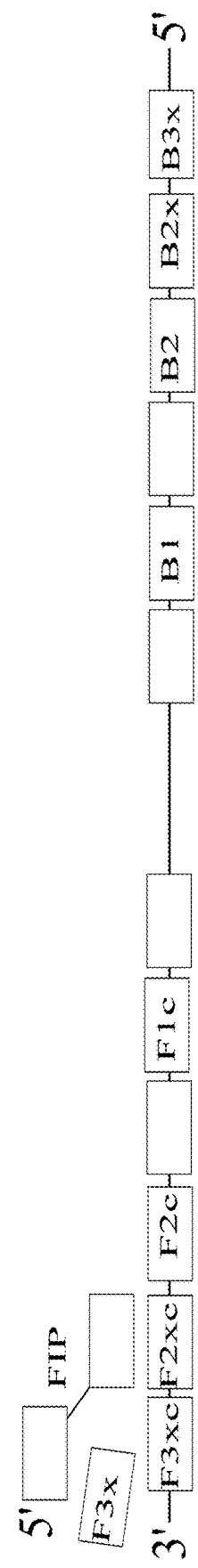

FIG 7
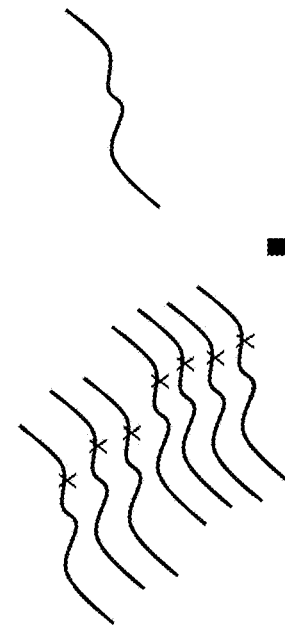
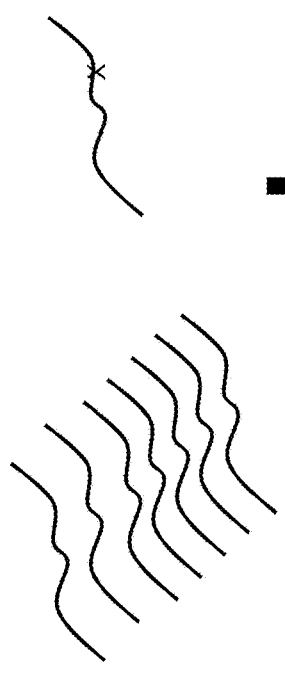

Figure 9. Target nucleic acid sequence

Sequence of Zika virus strain MR766, envelope encoding gene

>gi|226377833:977-2476 Zika virus, complete genome

ATCAGGTGCATTGGAGTCAGCAATAGAGACTTCGTGGAGGGCATGTCAGGTGGGACCTGGGTTGATGTTGTCTTGGAACATGGAGGCTGCGTTACCGTGATGGCACAGGACAAGCCAAC
AGTCGACATAGAGTTGGTCACGACGACGGTTAGTAACATGGCCGAGGTAAGATCCTATTGCTACGAGGCATCGATATCGGACATGGCTTCGGACAGTCGTTGCCCAACACAAGGTGAAG
CCTACCTTGACAAGCAATCAGACACTCAATATGTCTGCAAAAGAACATTAGTGGACAGAGGTTGGGGAAACGGTTGTGGACTTTTTGGCAAAGGGAGCTTGGTGACATGTGCCAAGTTT
ACGTGTTCTAAGAAGATGACCGGGAAGAGCATTCAACCGGAAAATCTGGAGTATCGGATAATGCTATCAGTGCATGGCTCCCAGCATAGCGGGATGATTGGATATGAAACTGACGAAGA
TAGAGCGAAAGTCGAGGTTACGCCTAATTCACCAAGAGCGGAAGCAACCTTGGGAGGCTTTGGAAGCTTAGGACTTGACTGTGAACCAAGGACAGGCCTTGACTTTTCAGATCTGTATT
ACCTGACCATGAACAATAAGCATTGGTTGGTGCACAAAGAGTGGTTTCATGACATCCCATTGCCTTGGCATGCTGGGGCAGACACCGGAACTCCACACTGGAACAACAAAGAGGCATTG
GTAGAATTCAAGGATGCCCACGCCAAGAGGCAAACCGTCGTCGTTCTGGGGAGCCAGGAAGGAGCCGTTCACACGGCTCTCGCTGGAGCTCTAGAGGCTGAGATGGATGGTGCAAAGGG
AAGGCTGTTCTCTGGCCATTTGAAATGCCGCCTAAAAATGGACAAGCTTAGATTGAAGGGCGTGTCATATTCCTTGTGCACTGCGGCATTCACATTCACCAAGGTCCCAGCTGAAACAC
TGCATGGAACAGTCACAGTGGAGGTGCAGTATGCAGGGACAGATGGACCCTGCAAGATCCCAGTCCAGATGGCGGTGGACATGCAGACCCTGACCCCAGTTGGAAGGCTGATAACCGCC
AACCCCGTGATTACTGAAAGCACTGAGAACTCAAAGATGATGTTGGAGCTTGACCCACCATTTGGGGATTCTTACATTGTCATAGGAGTTGGGGACAAGAAAATCACCCACCACTGGCA
TAGGAGTGGTAGCACCATCGGAAAGGCATTTGAGGCCACTGTGAGAGGCGCCAAGAGAATGGCAGTCCTGGGGGATACAGCCTGGGACTTCGGATCAGTCGGGGGTGTGTTCAACTCAC
TGGGTAAGGGCATTCACCAGATTTTTGGAGCAGCCTTCAAATCACTGTTTGGAGGAATGTCCTGGTTCTCACAGATCCTCATAGGCACGCTGCTAGTGTGGTTAGGTTTGAACACAAAG
AATGGATCTATCTCCCTCACATGCTTGGCCCTGGGGGGAGTGATGATCTTCCTCTCCACGGCTGTTTCTGCT (SEQ ID NO: 1)

Figure 10. LAMP primer set to target Zika envelope encoding gene.

Primer set:
ID:8   dimer(minimum)dG=-1.60

| label | 5'pos | 3'pos | len | Tm | 5dG | 3dG | GCrate | Sequence |
|---|---|---|---|---|---|---|---|---|
| F3 | 303 | 321 | 19 | 59.58 | -4.97 | -4.85 | 0.53 | GGGAAACGGTTGTGGACTT (SEQ ID NO: 2) |
| B3 | 503 | 521 | 19 | 59.74 | -5.70 | -4.06 | 0.53 | GCTTCCGCTCTTGGTGAAT (SEQ ID NO: 3) |
| FIP |  |  | 40 |  |  |  |  | CCGGTTGAATGCTCTTCCCGG-GCAAAGGGAGCTTGGTGAC (SEQ ID NO: 4) |
| BIP |  |  | 40 |  |  |  |  | GCTATCAGTGCATGGCTCCCA-GGGCGTAACCTCGACTTTCG (SEQ ID NO: 5) |
| F2 | 326 | 344 | 19 | 60.62 | -5.01 | -5.51 | 0.58 | GCAAAGGGAGCTTGGTGAC (SEQ ID NO: 6) |
| F1c | 377 | 397 | 21 | 65.28 | -6.28 | -6.98 | 0.62 | CCGGTTGAATGCTCTTCCCGG (SEQ ID NO: 7) |
| B2 | 482 | 500 | 19 | 59.89 | -6.26 | -4.79 | 0.58 | GGCGTAACCTCGACTTTCG (SEQ ID NO: 8) |
| B1c | 420 | 440 | 21 | 64.38 | -4.32 | -5.70 | 0.57 | GCTATCAGTGCATGGCTCCCA (SEQ ID NO: 9) |

| Name | Sequence | Tm°C | CG% | nt |
|---|---|---|---|---|
| LF | AACACGTAAACTTGGCACAT (SEQ ID NO: 10) | 60.1 | 40 | 20 |
| LB | AGCGGGATGATTGGATATGAA (SEQ ID NO: 11) | 65.6 | 42.9 | 21 |
| F3 | GGGAAACGGTTGTGGACTT (SEQ ID NO: 2) | 64.2 | 52.6 | 19 |
| B3 | GCTTCCGCTCTTGGTGAAT (SEQ ID NO: 3) | 64.7 | 52.6 | 19 |
| FIP | CCGGTTGAATGCTCTTCCCGGGCAAAGGGAGCTTGGTGAC (SEQ ID NO: 4) | 88.6 | 60 | 40 |
| BIP | GCTATCAGTGCATGGCTCCCAGGGCGTAACCTCGACTTTCG (SEQ ID NO: 5) | 85.5 | 57.5 | 40 |

Figure 11. Test constructs for Competitive MTA

ZIK5-FLF

ACTACTACTACT*GAATTC*AAGGATAAGCAGCCAATGATCAGGGAAACGGTTGTGGACTTTTTGGCAAAGGGAGCTTGGTGACATGTGCCAAGTTTACGTGTTCTAAGAAGATGACCGGGAAG
AGCATTCAACCGGAAAATCTGGAGTATCGGATAATGCTATCAGTGCATGGCTCCCAGCATAGCGGGATGATTGGATATGAAACTGACGAAGATAGAGCGAAAGTCGAGGTTACGCCTAA
TTCACCAAGAGCGGAAGCACTCCTGCTACG*GAATTC*GGAAATAAACGGCCCAACCCTCA (SEQ ID NO: 12)

ZIK5-RLF

ACTACTACTACT*GAATTC*AAGGATAAGCAGCCAATGATCAGGGAAACGGTTGTGGACTTTTTGGCAAAGGGAGCTTGGTGACTTGTGCATTTGAACCGTGTACTAAGAAGATGACCGGGAAG
AGCATTCAACCGGAAAATCTGGAGTATCGGATAATGCTATCAGTGCATGGCTCCCAGCATAGCGGGATGATTGGATATGAAACTGACGAAGATAGAGCGAAAGTCGAGGTTACGCCTAA
TTCACCAAGAGCGGAAGCACTCCTGCTACG*GAATTC*GGAAATAAACGGCCCAACCCTCA (SEQ ID NO: 13)

QUASR probes for native sequence (FLF) and sequence with reversed-LF tag region (RLF)

Zik5-FLF QUASR primer set:

Z5-FLF: (5-6FAM)-AACACGTAAACTTGGCACAT (SEQ ID NO: 14)
(3-IABkFQ)-TTGTGCATTT*ACC* (SEQ ID NO: 15) Tm:~41.5C, 13 bases Zik5-RLF QUASR primer set:

Z5-RLF: (5-Cy5)-TACACGGTTCAAATGCACAA (SEQ ID NO: 16)
(3-IABkRQSp)-ATGTGCCAA*TCCC* (SEQ ID NO: 17) Tm:~41.6C, 13 bases

Figure 13.
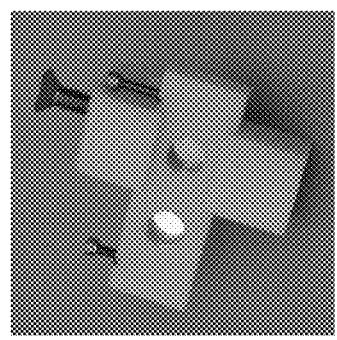
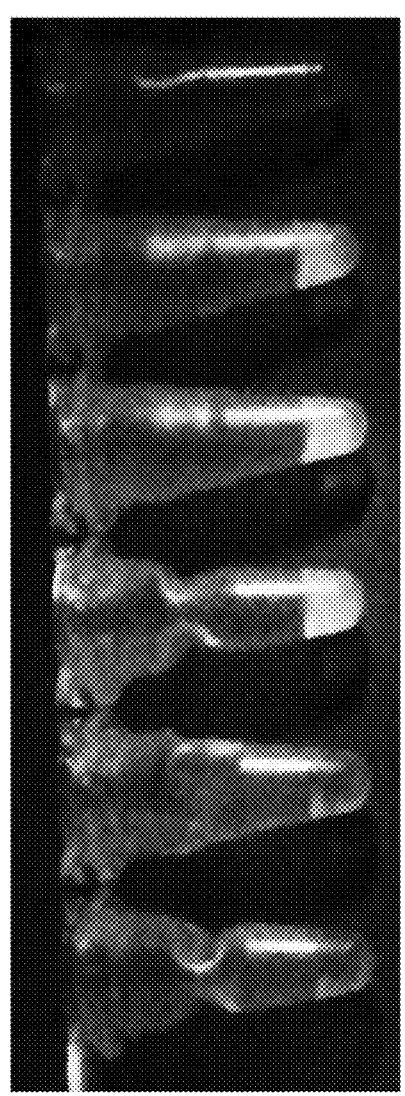
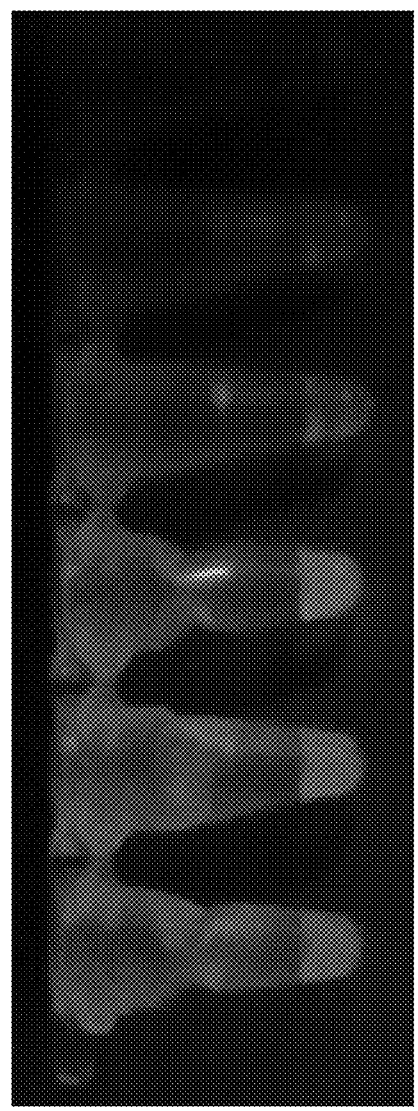

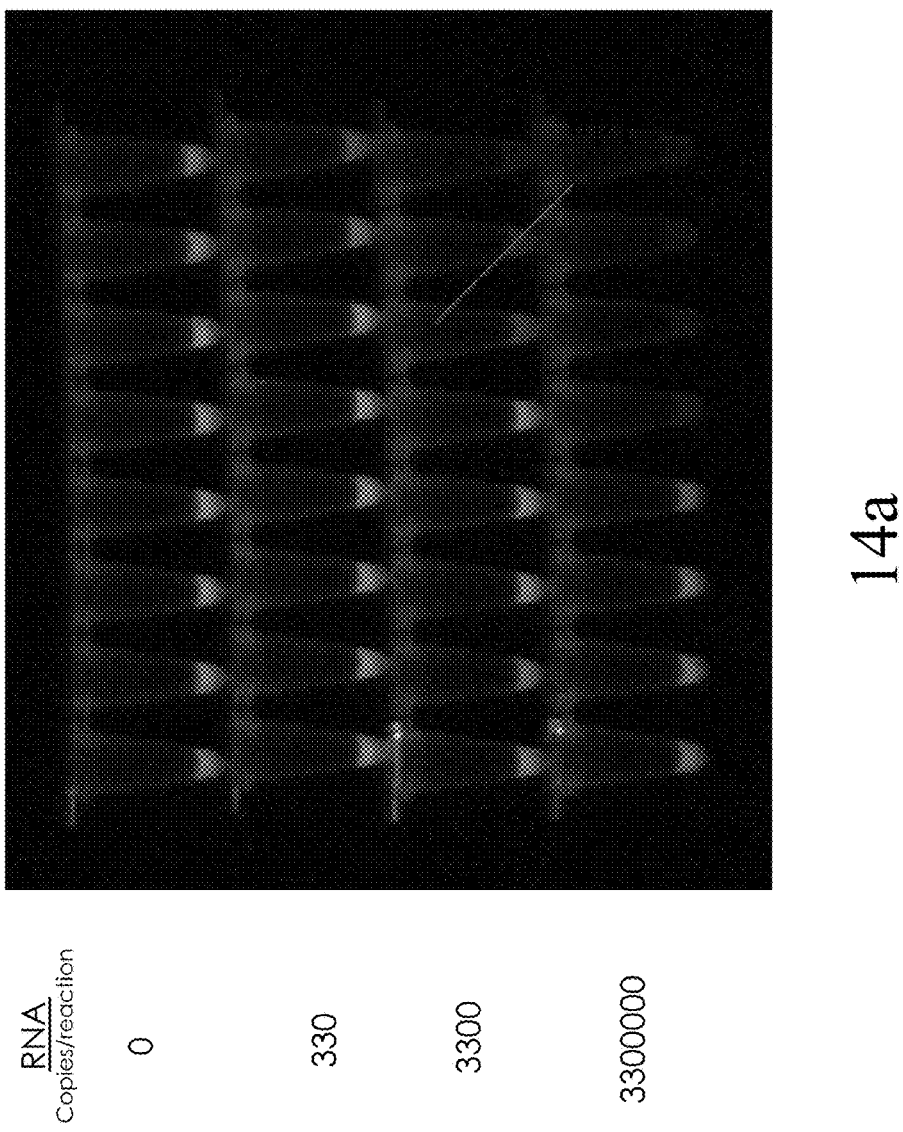
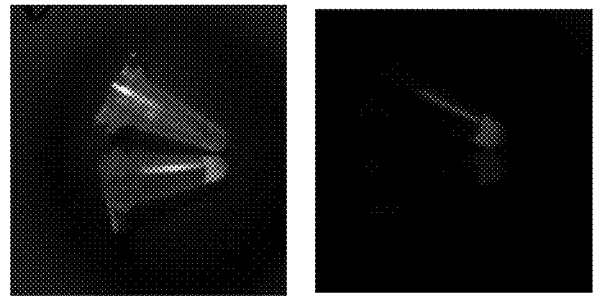
Figure 14.

METHODS FOR DIGITAL READOUT QUANTIFICATION OF NUCLEIC ACIDS

CROSS REFERENCE TO RELATED APPLICATION

The application claims the benefit of PCT/US17/45800, titled "METHODS FOR DIGITAL READOUT QUANTIFICATION OF NUCLEIC ACIDS," filed Aug. 7, 2017, which claims priority to U.S. provisional application No. 62/371,555, titled "METHOD FOR DIGITAL READOUT QUANTIFICATION OF NUCLEIC ACIDS," filed Aug. 5, 2016. Both are incorporated by reference herein in their entirety.

FIELD OF INVENTION

The invention is related to methods of digital readout quantification of nucleic acids that provide a high degree of false positive discrimination and require low-power implementation.

BACKGROUND OF THE INVENTION

The invention relates generally to point-of-care diagnostic technology for detection of specific nucleic acids. More specifically, the invention relates to improvements to nucleic acids analysis based on modification to the loop-mediated isothermal amplification (LAMP) reaction, wherein quantitation is achieved without the need for continuous monitoring of the reaction and the end-point readout is amenable to visual inspection.

There is continuing need for advancements in point-of-care diagnostic device technologies. For resource-limited settings, diagnostic technologies that are low cost and have low power requirement are very valuable and may have a wide variety of uses. For example, such a technology may enable quick and low-cost assessment of infection by specific viruses, bacteria, etc. It may also be used to test water sources for cleanliness, test livestock and animals for infectious agents, and test food to ensure food quality and safety.

However, quantitation remains limited in existing low-cost and low-power devices. Existing low-cost and low-power devices are either not capable of sufficient quantitative differentiation or lack the required specificity for the application. For example, responding to Dengue viral load when Zika viral load is of interest. Quantitative assessment of infection or microbial populations is valuable for numerous applications, including: ensuring regulatory compliance for public health standards, quantifying exposure to waterborne illnesses, and tracking effectiveness of mitigation strategies (for example, HIV treatment in patients.)

Various nucleic acid amplification techniques offer great potential regarding sensitivity and selectivity, and a vast number of assays have been successfully deployed. In general, when primers have been sufficiently well developed, these assays are very selective. These assays may also be highly quantitative, using techniques such as quantitative polymerase chain reaction (qPCR) and digital polymerase chain reaction (dPCR).

For qPCR, the emergence of a reaction is monitored continuously to determine quantity of analyte in the reaction, whereas the speed to reaction detection corresponds to concentration of analyte. This approach requires continuous monitoring of the reaction that requires more power and complexity. For dPCR, a single sample is partitioned into hundreds or thousands of individual reactions, adding to system complexity.

One major drawback of these approaches is the reliance on thermal cycling, which requires the use of precision cyclers to heat and cool the reaction to achieve the required temperatures of various steps of PCR. This requires continuous and reliable power.

Another drawback of PCR based approaches is that the results are not possible for naked eye readout and require relatively expensive readout optics. In the case of qPCR, unless the user wants to continuously watch the reaction until a certain optical characteristic has been achieved, naked eye readout is not an option. dPCR is also inaccessible to naked eye readout either, since the quantity of reactions within the hundreds to thousands of wells is used collectively, with reference to statistical relationships.

Another amplification technology known as loop-mediated isothermal amplification (LAMP) offers advantages in power consumption and readout cost/complexity over PCR based approaches. The LAMP reaction is based on isothermal enzymes with strand displacement capability, eliminating the need for thermal cycling. This lack of thermal cycling facilitates battery-powered devices and potentially lowers device cost.

Another advantage of LAMP-based diagnostic methods over PCR-based methods is that its reaction product may dramatically alter the chemical composition of the reaction vessel such that changes in turbidity, colorimetric dyes, or even pH can easily be seen with the naked eye or low-cost cameras.

There is one known approach for quantitative, end-point assessment via LAMP. This approach uses an intercalating dye, common to other quantitative LAMP assessments, but instead of correlating the time of reaction detection with analyte concentration, the device works through diffusion. The reaction is allowed to diffuse down a narrow column such that the length of the diffusive incursion relates to the time of the reaction initiation, which in turn relates to the reaction's analyte concentration. The intercalating dyes known in the literature are fluorescent, so although this method can be used for visual inspection, it would generally require a relatively dark environment with special illumination sources and filters (for example, special readout glasses) to make the assessment. Another difficulty with this system is that there is no way to discriminate false positive reactions from true positives. This creates a problem for assay specificity and sensitivity.

Whereas LAMP based diagnostic methods provide a significant advantage over other diagnostic methods based on PCR, it has drawbacks as well. LAMP based diagnostic methods are usually limited in quantitative capacity as LAMP is in general not as accurate as qPCR or dPCR. LAMP also has a high rate of false positives.

Accordingly, it is desirable to provide improved methods that provide easy readout, require low power implementation and are capable of a high degree of false positives discrimination that overcome drawbacks and inadequacies of known methods.

SUMMARY OF THE INVENTIONS

Generally speaking, in accordance with an embodiment of the invention, methods of providing quantitative assessments using visual inspection or without requiring constant monitoring of the reaction are provided.

An embodiment of the invention provides for performing a two-stage multiple-threshold array (MTA). By creating a two-step method, with the first stage focused on target specification and the second stage focused on target detection through the detection of a secondary sequence, the current invention is able establish thresholds to produce digital readout. Using this method, rapid and sensitive visual detections may be achieved and performed in real time, enabling quantitative applications without needing specialized or expensive instruments.

Another embodiment of the invention provides a competitive MTA method through the use of a tag. By incorporating fluorescence-quenching technique to determine amplification specificity, a sensor with digital readout may also be accomplished.

Still other objects and advantages of the invention will in part be obvious and will in part be apparent from the specification. Other features and advantages of this invention will become apparent in the following detailed description of exemplary embodiments of this invention with reference to the accompanying drawings.

BRIEF DESCRIPTION OF THE DRAWINGS

For a fuller understanding of the invention, reference is made to the following description taken in connection with the accompanying drawing, in which:

FIG. 3 is an illustration of a part of the reaction principle of the embodiment of FIG. 1;

FIG. 7 is an illustration of competitive LAMP reaction resulting in different fluorescence;

FIG. 9 shows an example target Zika nucleic acid sequence;

FIG. 10 shows a LAMP primer set to target Zika envelop protein gene;

FIG. 11 shows the test constructs for competitive MTA;

FIG. 13 shows visual result of fluorescence;

FIG. 14 shows visual identification of digitization;

DETAILED DESCRIPTION OF THE PREFERRED EMBODIMENTS

Figure 1:
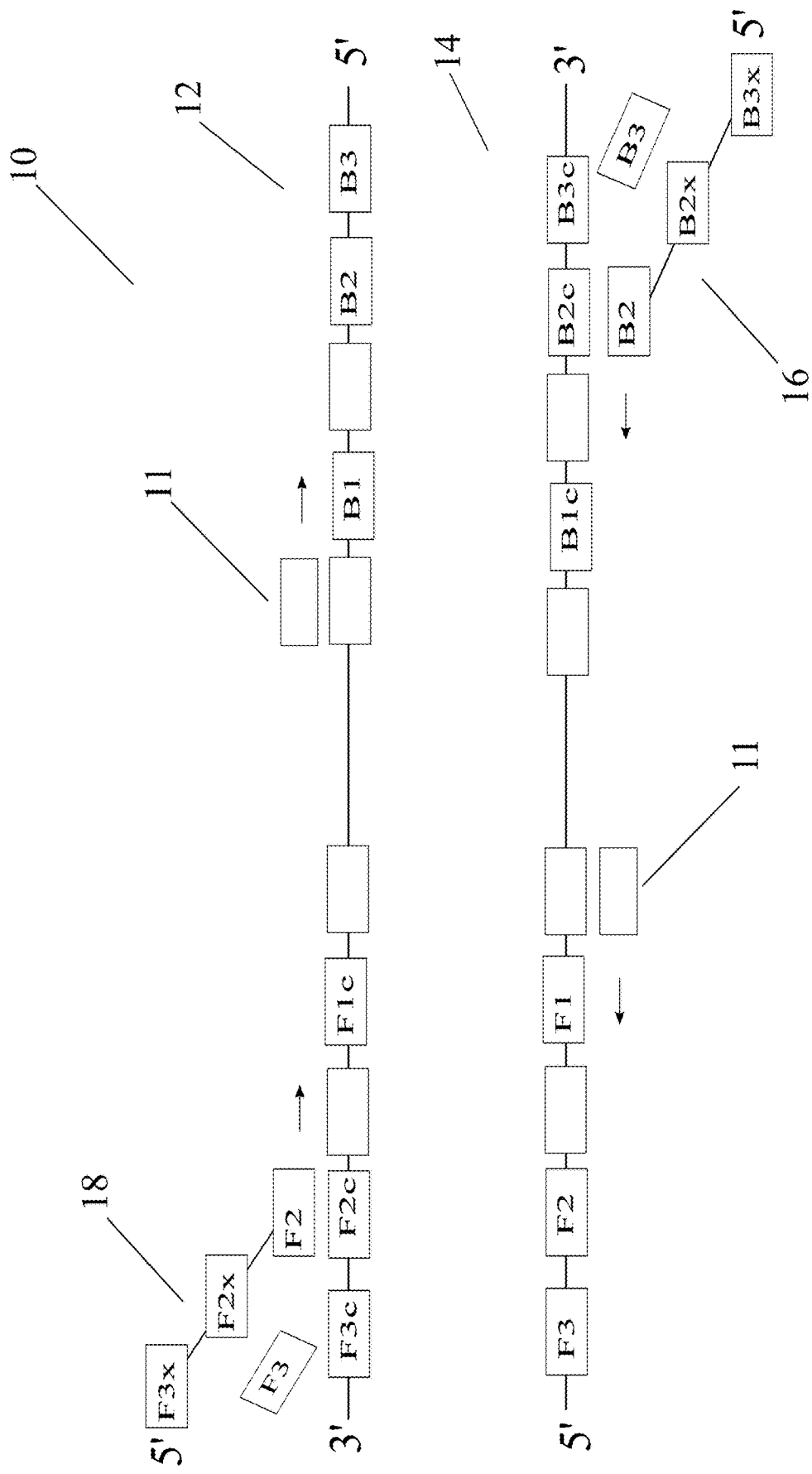
FIG. 1 is an illustration of initiation of the reaction principle in accordance with an embodiment of the invention.

The invention generally is directed to diagnostic methods using nucleic acid amplification technology, more particularly to loop-mediated isothermal amplification (LAMP) based diagnostic methods that enable digital readout endpoint quantitative tests that may be amenable to naked eye readout. These methods not only have a low power requirement but also provide a high degree of specificity and sensitivity. As discussed above, whereas PCR based diagnostic methods are effective, because of the high cost of equipment, power requirement and need to continuously monitor the result, LAMP based diagnostic methods may be preferred in certain situations. For example, when amplification is being performed outside of a laboratory at point of care, LAMP based diagnostic methods may be preferred.

Two methods for achieving quantitative, end-point nucleic acid detection via LAMP are disclosed herein. Both methods feature multiple threshold array (MTA) assay. A MTA includes a set of independent reactions that work together to enable quantification. The basic concept of MTA derives from electrical engineering, where a device known as an analog to digital converter (ADC) compares an input voltage to an array of voltage thresholds. For each threshold that is exceeded by the input voltage, a logic value of 1 is placed on an output terminal. For example, a 3-volt signal, compared with a 4 digit ADC with threshold voltages evenly spaced at 0, 2.5, 5, and 10 volts, will yield a 1-D array of output logic of 1,1,0,0. This indicates that the input signal is greater than 0, greater than 2.5, less than 5, and less than 10 volts. By adding additional thresholds and logical comparisons, the resolution of the ADC can be further improved.

Using this core concept, each of the quantification methods of the present invention is an array of reaction wells that are setup with variable sensitivity to a given input level of analyte. The main difference between the methods is the manner in which the thresholds, and therefore differential sensitivity, is established. A second difference in the two methods is their readout visualization. Two-stage MTA can result in bolometric readout by the naked eye, requiring no accessory illumination source or filter. The competitive MTA, on the other hand, requires fluorescent readout, thus requiring illumination and/or filtration accessories.

Two-Stage MTA

In one embodiment of the present invention, a two-stage MTA may be used to provide visual quantitation readout. During the first stage of the reaction, molecular species may be created and amplified, which then may be recognized in a second stage. The first stage of the reaction may aim to amplify target sequences and the second stage of the reaction may utilize LAMP techniques to amplify target indicators for easy quantification. All the primers used in the current embodiment should be designed with attention to recommended LAMP primer design parameters, including segment melting temperatures, optimal spacing, etc.

Figure 2:
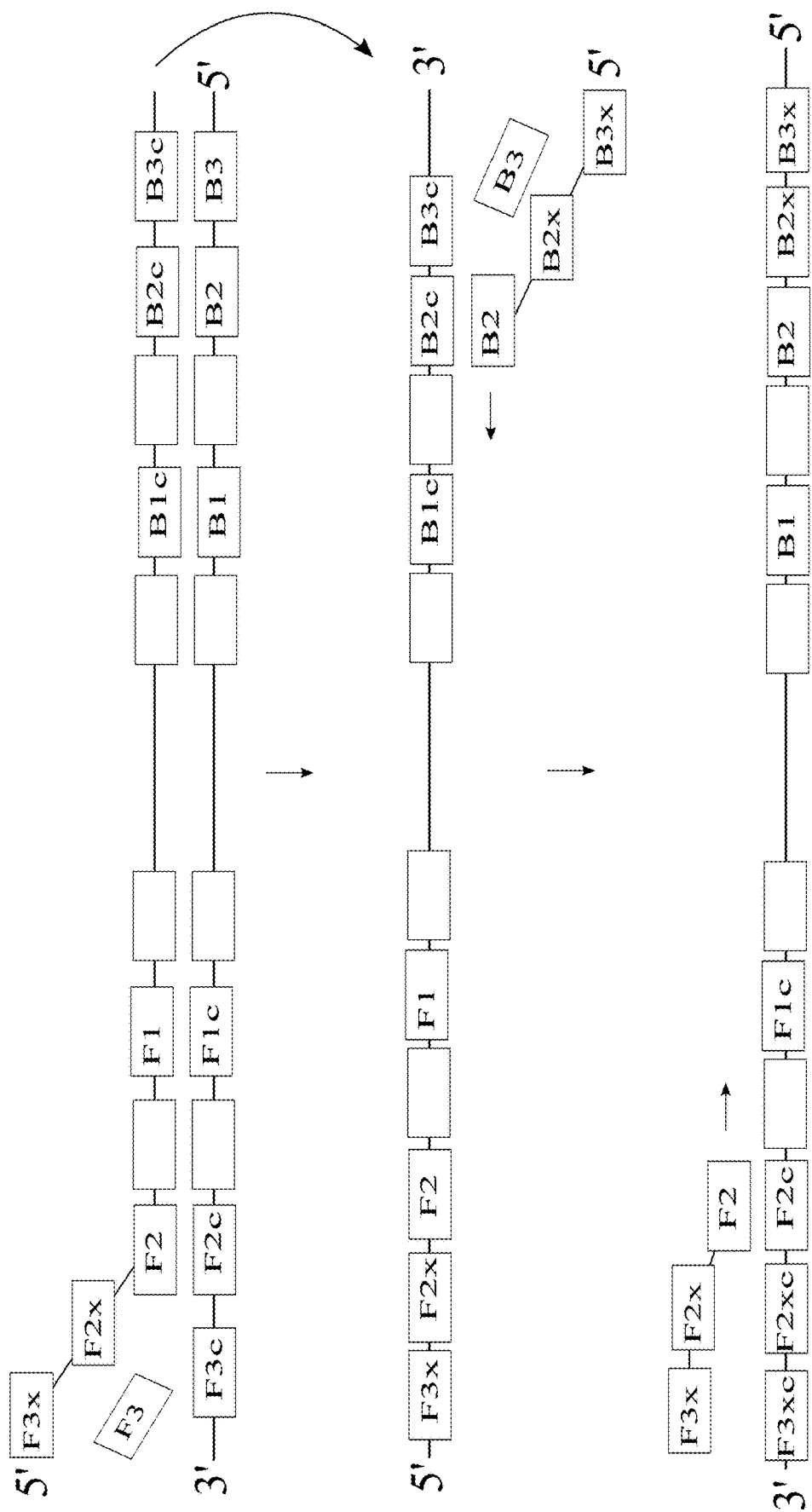
FIG. 2 is an illustration of a part of the reaction principle of the embodiment of FIG. 1.

Reference is made to FIGS. 1-3. FIG. 1 illustrates a double-stranded DNA 10 separated into two single strands 12, 14 by breaking the hydrogen bonds between the two strands during a denaturation step. This step may be achieved by various approaches, such as through thermal means. In one example, denaturation is done by heating to 95° C. for 5-10 minutes. Alternatively, accessory primers, such as loop or swarm primers, may be used as in conventional LAMP reactions, commonly taking place around 60-65° C.

The first stage may also proceed without an explicit denaturation step. However, without denaturation, the overall reaction efficiency may decrease and result in lower limits of detection. Higher temperatures may also help increase target specificity and improve amplification of non-denatured templates.

Regardless how the two single strands 12, 14 may be separated, they serve as templates, to which primers FXP 18 and BXP16, may anneal. Both FXP and BXP primers may have a 3' region that contains a complementary sequence to the targeted sequence to provide target specificity and may also contain a 5' overhang that introduces a secondary sequence. Specifically, FXP 18 may comprise three domains, and they may be separated by linker bases. The first domain is a standard LAMP F2 region, similar to a conventional FIP primer, complementary to F2c of strand 12. This allows the FXP primer to anneal to the traditional LAMP F2c region. The second domain is the F2x region. This may contain a secondary sequence and not complementary to strand 12. The secondary sequence may serve as a recognition sequence for the second stage of this method. The third domain, F3x, may contain a sequence that enables separation of double stranded DNA during stage two of the reaction. F3x may be analogous to F3 in the conventional LAMP reaction.

Similarly, BXP 16 contains B2, which is complementary and anneals to B2c region of strand 14. In addition, BXP 16 also may contain B2x and B3x. B2x may include a secondary sequence. The secondary sequence of BXP 16 may or may not be identical to the secondary sequence of FXP. B3x may be analogous to B3 in the conventional LAMP reaction. A stem primer 11 may also be used, which may anneal to each template strands 12, 14, adjacent to either the F1 or B1 regions, and extending towards the F1 or B1 regions.

FIG. 2 illustrates the continuation of the reaction initiated in the first stage to produce amplicons retaining the native sequence between F2 and B2 while incorporating the F2x/B2x and F3x/B3x. The FXP and BXP primers have annealed to their targets and have extended in the 5' to 3' direction to create double-stranded sequences such as double-stranded DNA 20. Double-stranded DNA 20 includes FXP initiated strand with a sequence that is complementary at its 3' end to the template strand from the native DNA and 5' end that contains the secondary sequence. Similarly, another double-stranded DNA including BXP initiated strand with a sequence that is complementary at its 3' end to the other template strand from the native DNA and 5' end that contains the secondary sequence, may be created.

To separate the double stranded DNA 20, F3 and B3 may be used to bind according to conventional LAMP reactions, enabling displacement of the FXP initiated strand 22 and BXP initiated strand (not shown). As the reaction continues, the free FXP/BXP initiated strands may bind with free BXP 24 and FXP 25 to produce additional amplicons that contain the target sequence, as well as the secondary sequence. At the end of the first stage of the two-stage process, quantities of the double stranded DNA 30 shown in FIG. 3 may be created. The double-stranded DNA 30 differs from the native double-stranded DNA 10 shown in FIG. 1 because it has incorporated F2x/B2x and F3x/B3x and F3/B3 has been eliminated. At this point, the second stage of the MTA may begin.

The goal of the second stage of the reaction is to amplify the secondary sequence for detection. A conventional LAMP reaction may proceed with standard LAMP primers, FIP/BIP and Fx/Bx pairs, designed to work with F2x and F3x segments. To facilitate the separation of double-stranded DNA, loop, swarm or stem primers may be used to increase LAMP's capacity for amplifying the F2x and F3x incorporated double-stranded DNA. Alternatively, as mentioned above in the denaturation step of the first stage of the reaction, the double-stranded DNA 30 may be denatured through other means, such as high temperature.

Once separated, inner primers FIP and BIP designed to amplify the secondary sequence may anneal to the single strands and initiate DNA synthesis. Using LAMP in the second stage of the reaction may enable the synthesis of large amounts of the secondary sequence quickly and efficiently, which may be carried out in a manner that produces visible products using indicator dyes. To provide visual quantitation readout, dyes such as hydroxyl naphthol blue (HNB) may be used. PH indicator dyes such as cresol red, may also be used.

The whole two-stage reaction takes place at a single temperature, preferably around 65° C. However, the temperature may be altered to optimize the reaction depending on the particular target and primers. Although not required, it may also be possible to elevate the temperature periodically to promote double-stranded DNA dissociation.

Using the two-stage reaction, a MTA may be set up by arranging an array of wells, each well containing primers used both in the first stage and the second stage of the reaction. The concentration of primers used in the first stage vary between wells, while every well contains the same, preferably high, concentration of primers used in the second stage to allow efficient amplification of the secondary sequence to produce visual quantitation. The different concentration of first stage primers enable only certain wells to detect low concentration of analytes, while all wells may be capable of detecting high concentration of analytes. Wells with high concentration of primers used in the first stage may react with target DNA and produce the amplicon with target sequence incorporated, even when the target DNA is of low concentration. In contrast, wells with low concentration of first stage primers may not be able to sufficiently react with low target DNA concentration. Since the second stage primers anneal and amplify the amplicons from the first stage, i.e. modified strands with secondary sequence incorporated, if the concentration of amplicons from the first stage is low or insufficient, the resulting visual signal may be low or nonexistent. In comparison, if ample amplicons from the first stage exist to react with second stage primers, a visual signal, such as color change, may be readily produced. Because of the varying concentrations of the first stage primers producing varying level of amplicons, an array of visual indicators may result. In this way, digitization may be accomplished as the wells produce end-point, quantitative naked-eye visualization of a sample's target concentration. Depending on the performance of particular primers, it may be necessary to replicate wells to provide reliable results.

Competitive MTA

In another embodiment of the present invention, a competitive MTA may be used to provide visual quantitation readout. Specifically, the specificity of a reaction maybe quantified by the presence of a tag. If the LAMP reaction is specific, the tag may be incorporated into the growing amplicons. If LAMP reaction is non-specific, the tag may not be incorporated into the growing amplicons, or may be inefficiently incorporated.

Figure 4:
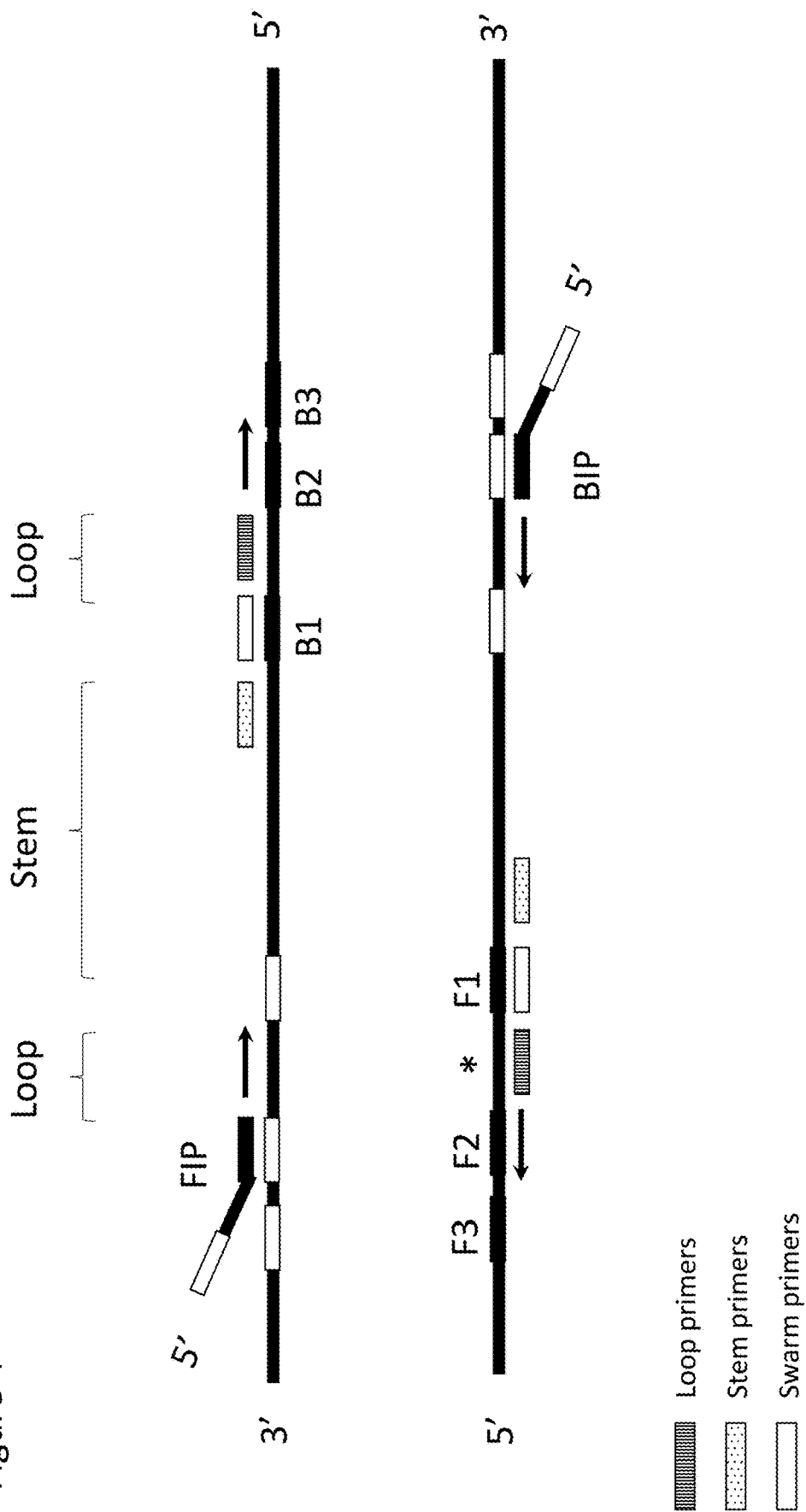
FIG. 4 is an illustration showing various regions for tags.

FIG. 4 illustrates the preferred locations for tags in reference DNA sequences. Ideal locations may include the areas labeled as "loop", "stem" and also F1. Many of the examples used in this application use tags in the loop region and corresponding loop-tagging primers. It is understood that the tags may locate in other regions, and corresponding primers may be used accordingly.

To set up a competitive environment, a reference sequence is designed to be identical to the target sequence with the exception that one or more tags. Each tag may be any sequence that does not interact with any other component of the reaction. Preferably, the tag contains a sequence that is in the reverse orientation as the target sequence in the same location. For example, a reference sequence designed to make use of the loop region will have identical target sequence, except in the designated loop region. This reverse sequence in the loop region prevents loop primers designed for the target sequence from annealing. In contrast, a new primer, designed in reverse, may bind to the reverse sequence, establishing the tag, which differentiates between the target sequence and the reference sequence. Loop primers designed to anneal to target sequence is termed forward loop-forward (FLF) primers. Loop primers designed to anneal to the reference DNA (with reversed sequence) is termed reverse loop-forward (RLF). During LAMP, primers may be incorporated into amplicons thus decreasing the concentration of free primers. By measuring the resulting free primers, forward or reversed, available, the specificity of the amplification may be determined.

It is possible to design a reference sequence that's not

To visualize the result of the competitive assay, a primer may be tagged with a fluorophore and the reaction may take place in the presence of a complementary sequence that includes a quencher molecule positioned such that when the primer and the complementary sequence anneal to each other, fluorescence may be quenched by the quencher. The complementary sequence and the quencher may be added after the LAMP reaction or may be added at the start of the reaction at room temperature along with other primers. When added at the same time, at room temperature, primer and its quencher may anneal. However, at LAMP reaction temperatures, the strands would be come unbound, freeing the primers to bind and become incorporated into amplicons if the amplicons contain suitable binding sites. Once the results are cooled to room temperature, a specific LAMP reaction would successfully incorporate primers and the fluorophore tag into amplicons created, leaving few free tagged primers to anneal to their complementary sequence and the quenching module. If the reaction is not specific, fluorophore tagged primers would remain free and readily anneal to the complementary sequence, thus quenching the fluorescence.

Figure 5:
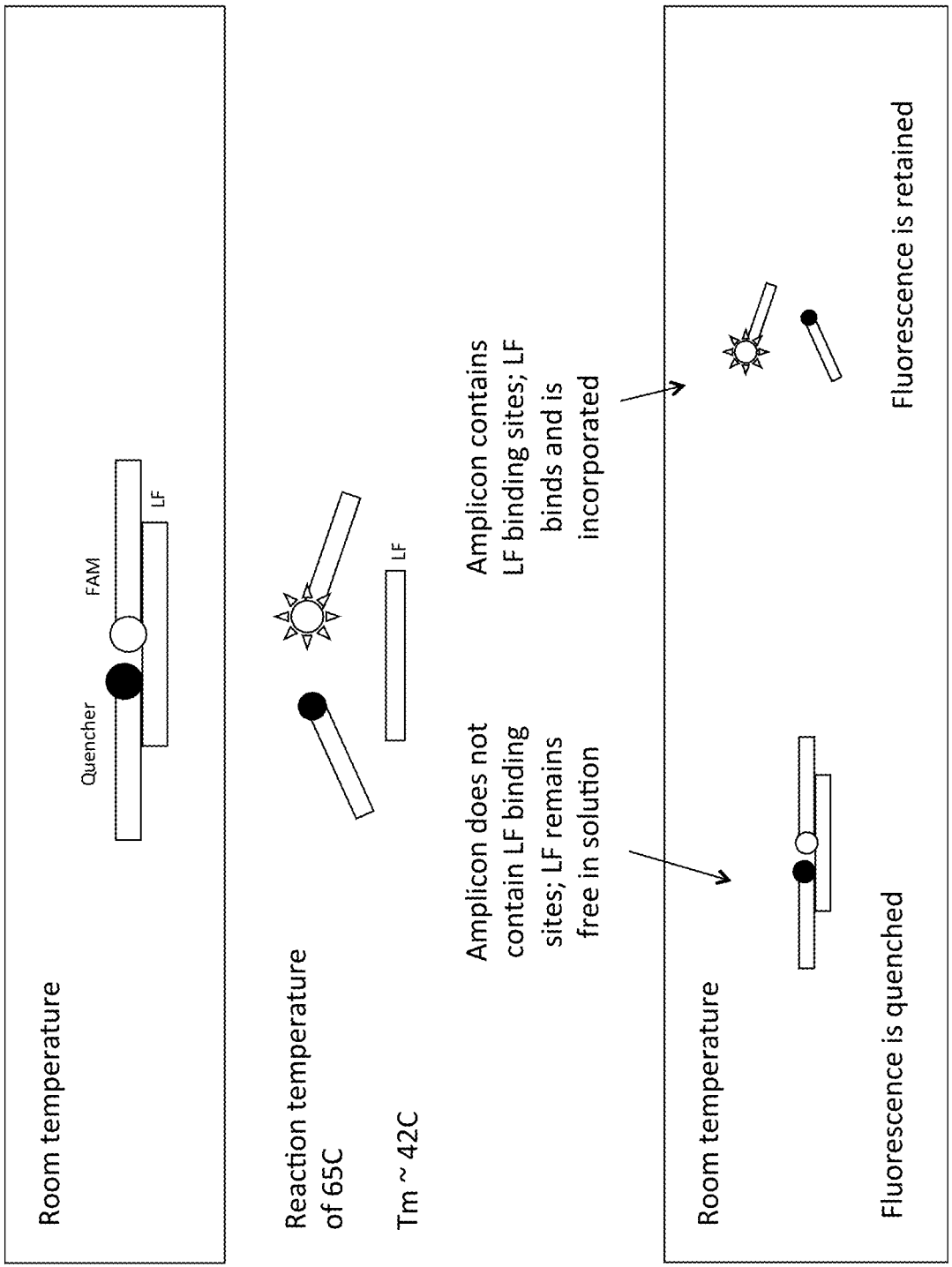
FIG. 5 is an illustration showing an example of fluorescence production from a LAMP reaction.

Alternatively, instead of using a primer tagged with a fluorophore and the reaction is carried out in the presence of a complementary sequence that includes a quencher molecule, a fluorophore-quencher pair not attached to the primer may be used. Reference is made to FIG. 5, which illustrates the use of a fluorophore-quencher pair with LF primers. At room temperature, LF primer serves as the annealing target and binds to the fluorophore-quencher pair. When the temperature is raised to LAMP reaction temperature of 65° C., LF primer separates from the fluorophore-quencher pair and is free to participate in the LAMP reaction. If amplicons contain LF binding sites (specific reaction), LF primers bind and are incorporated into growing amplicons so that the concentration of free LF primer is greatly diminished at the end of the reaction. Subsequently, when the reaction mixed is subsequently cooled, few LF primers remain for quenching and thus bright fluorescence is observable. However, if the present amplicons do not contain LF binding sites, the non-specific reaction is non-specific and does not promote incorporation of the LF primer into amplicons even if LAMP reaction takes place. LF primers remain in sufficient quantity and can template the annealing of the fluorophore-quencher pair. Thus, fluorescence is quenched.

Either of the two methods of fluorescence reporting may be used in the embodiment of the current invention even though fluorescence is quenched differently. In the first method disclosed, fluorescence remains when the fluorophore-tagged primer is incorporated into the amplicon, while in the second method, the fluorophore is never incorporated into the amplicon, but the presence or lack of appropriate primers to serve as the annealing target for the fluorophore and the quencher determines whether fluorescence is quenched.

Figure 6:
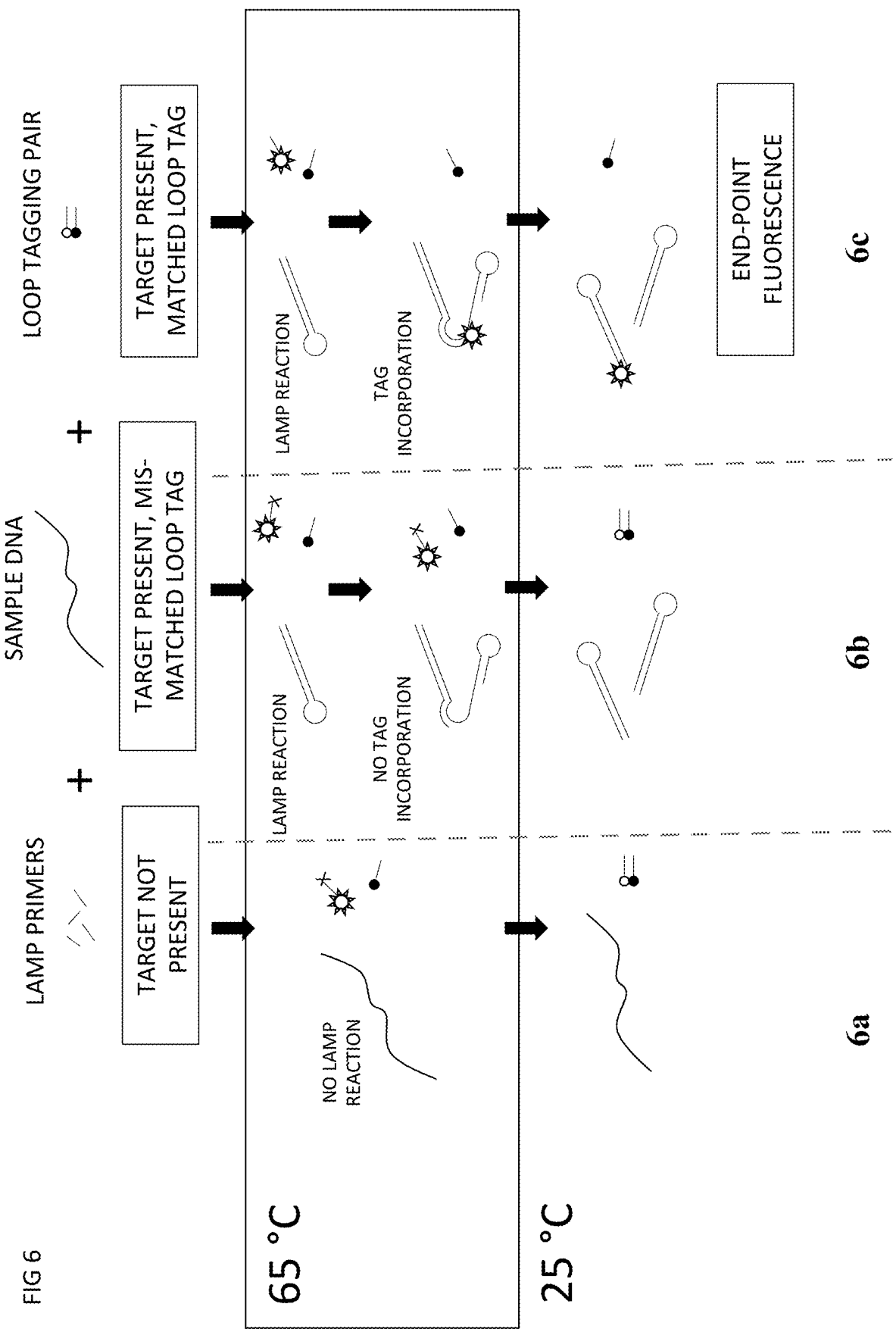
FIG. 6 is an illustration of fluorescence reporting using loop tagging.

FIG. 6 illustrates fluorescence reporting in three different scenarios using a tag in the loop region. In this example, the loop tagging pair refers to the use of a fluorophore-tagged LF primer and its complementary sequence and quencher. In the first scenario 6a, the nucleic acid target is not present in the sample. No LAMP reaction takes place. Fluorescence is quenched as no fluorophore-tagged LF primer is incorporated into the amplicons.

In the second scenario 6b, the target is present but the loop region is mis-matched with respect to the loop tagging primer set. Because the target it present, LAMP reaction takes place. But because of the mismatch, no LF primer is incorporated into the amplicons despite of a LAMP reaction. Again, fluorescence is quenched.

In the third scenario 6c, the target is present and the loop region is matched to the loop tagging probe set. The fluorophore-tagged primer is successfully incorporated into the amplicons. Upon cooling, no LF primer is left free in the solution to anneal to the complementary sequence. Therefore, quenching cannot take place. Thus, fluorescence is observed at the end of the reaction at room temperature. The presence of fluorescence is an indication of a positive reaction with the loop region in a specified orientation.

Using the techniques described above, digital readout may be accomplished by setting up a competitive reaction within a reaction vessel and using at least one color fluorescence tag. In accordance with one embodiment of the invention, an array of wells may be preloaded with varying amounts of reference target. The reference target is preferably identical to the sample target sequence except that the tag region binds in the reverse orientation while the sample target contains the target region in forward orientation. The reference target serves as competition against sample targets added.

Each well may also contains primers for both the reference target and the sample target. Because the reference target and the sample target are almost identical except for a reversed target region on the reference target, their primers are also almost identical except that the target region on the primer for the reference target is in reverse orientation and the target region on the primer for the sample target is in forward orientation. Each primer may include a different color fluorophore. In one embodiment of the current invention, as illustrated in FIG. 7, two fluorophore-quencher probe pairs are used, one for the sample sequence and the other for reference sequence. The advantage of using a single color fluorescence is simplified instrumentation or readout. The advantage of using a two-color approach is increased robustness, as, for example, lack of color production can result from competitive inhibition or from improper reaction conditions.

In accordance with the invention, the sample is loaded into the wells with various amounts of reference target along with the probe pairs. In each well, sample targets compete against reference targets for available amplification resources. When more reference targets exist in a well than sample targets, more amplicons incorporating the reference target primers are synthesized. Thus, upon cooling when each unincorporated primers would anneal to its complementary quencher sequences, the tagged fluorophore would be quenched and only primers that have been incorporated would retain its fluorescence. Depending on how much and which of the fluorophore-tagged primers are incorporated, each well would produce a different color effect.

As illustrated in the sample shown in FIG. 7, the fluorophore on the sample LF 71 primer is green, whereas the fluorophore on the reference LF primer 72 is red. When the concentration of sample DNA is much greater than the concentration of the reference DNA, the dominant LAMP reaction would produce more amplicons that may react with the red fluorophore. In contrast, when the concentration of reference DNA is much greater than the concentration of the sample DNA, there will be a greater propensity for the reaction to produce amplicons that react with the green fluorophore. As noted above, although the example illustrated in FIG. 7 uses a tag located in the loop region, it is understand that tags located in other regions and corresponding primers may be used to practice the current invention.

Figure 8:
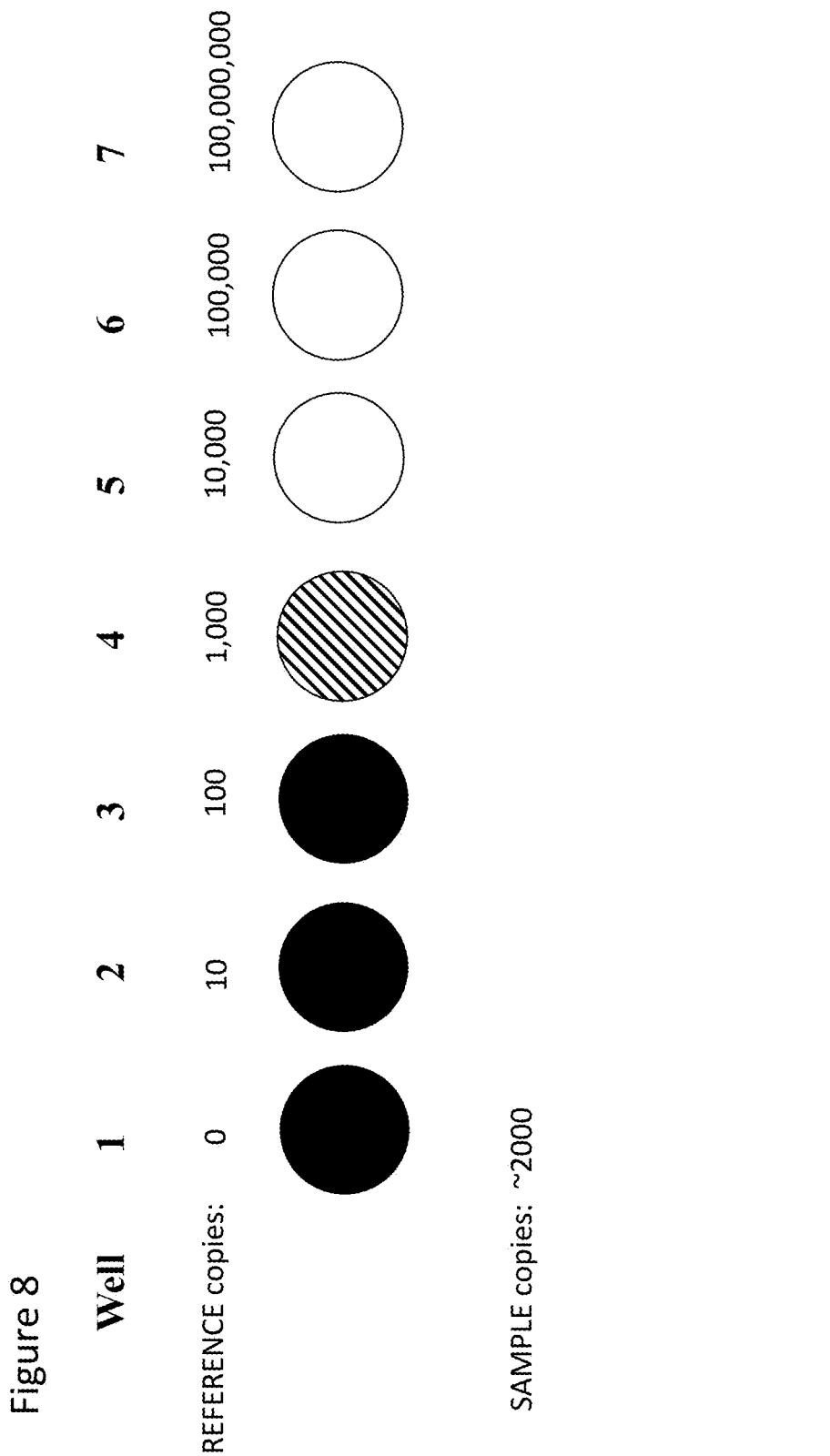
FIG. 8 shows a color range reference example.

When an unknown sample is loaded into a set of wells, pre-loaded with known amounts of reference sequence, then the competitive reactions can produce fluorescence responses in a threshold fashion. For example as illustrated in FIG. 8, 2000 copies of the sample in well 1, which has no competing reference sequence, would be preferentially amplified, therefore showing the strongest red fluorescence. Whereas 2000 copies of the same sample competes only imperfectly in well 4, which contains 1000 copies of the reference sequence. In well 6, where there are 100,000 copies of reference sequence, the sample sequence is only infrequently amplified in comparison with the reference sequence. In this case, the reference sequence is associated with fluorescence in the green. Therefore, based on the brightness and the color of the fluorescence shown, one may quantify the amount of sample sequence added given known reference sequence quantity.

Increased seeding concentrations of reference target may establish a thresholding mechanism such that the wells that show appreciable green fluorescence are logic outputs of '1', analogous to the analog-to-digital converter described earlier. A panel of such wells, properly seeded with reference levels of target sequence, may enable a digitized readout that may be assessed using inexpensive tools, such as flashlights or filtered glasses. Although this approach may require fluorescence equipment for readout, it may be highly immune to false positive reactions.

Example: Zika Virus

Reference is made to FIGS. 9-11. An exemplary assay was designed to target nucleic acids from the Zika virus to demonstrate the current invention. FIG. 9 shows the selected sequence used in this example, which codes for an envelope protein. The particular region targeted for the competitive assay of the current invention is shown in bold, and underlined. Other nucleic acid target may be used. FIG. 10 lists the primer sets used in the example to target Zika envelope encoding gene. Standard LAMP primer design tools (Eiken Chemical Co. PrimerExplorer, found at primerexplorer.jp/e/intro/) were used to design sequences targeting the Zika envelope-encoding gene.

In FIG. 11, the constructs for reference sequence and target sequence are included. The sequences contain identical target nucleic acids, as shown in FIG. 9, with the exception that one sequence contains the region that forward Loop primers (LF) bind to is of reversed sequence for the second sequence (RLF). The other sequence contains the Loop primer target region in forward orientation (FLF).

Also shown in FIG. 11 are primers for each sequence. Z5-FLF contains the forward loop primer (FLF), exactly as the standard LF primer of FIG. 10, except that a fluorescent molecule (green fluorescent fluorophore, fluorescein-based FAM) has been attached to the 5' end. The probe is complemented by a segment with a 3' quencher such that, at temperatures below the annealing (in this case, about 42 C), the quencher is attached. During the reaction, the strands are separated and FLF is free to participate in the LAMP reaction. An exemplary RLF is also shown. In this case, a red fluorophore (Cy5) is attached to the 5' end. Its complementary sequence also contains a quencher on its 3' end. These two probe pairs are thus able to differentiate amplification targets by the orientation of the LF region of the target nucleic acid.

Figure 12:
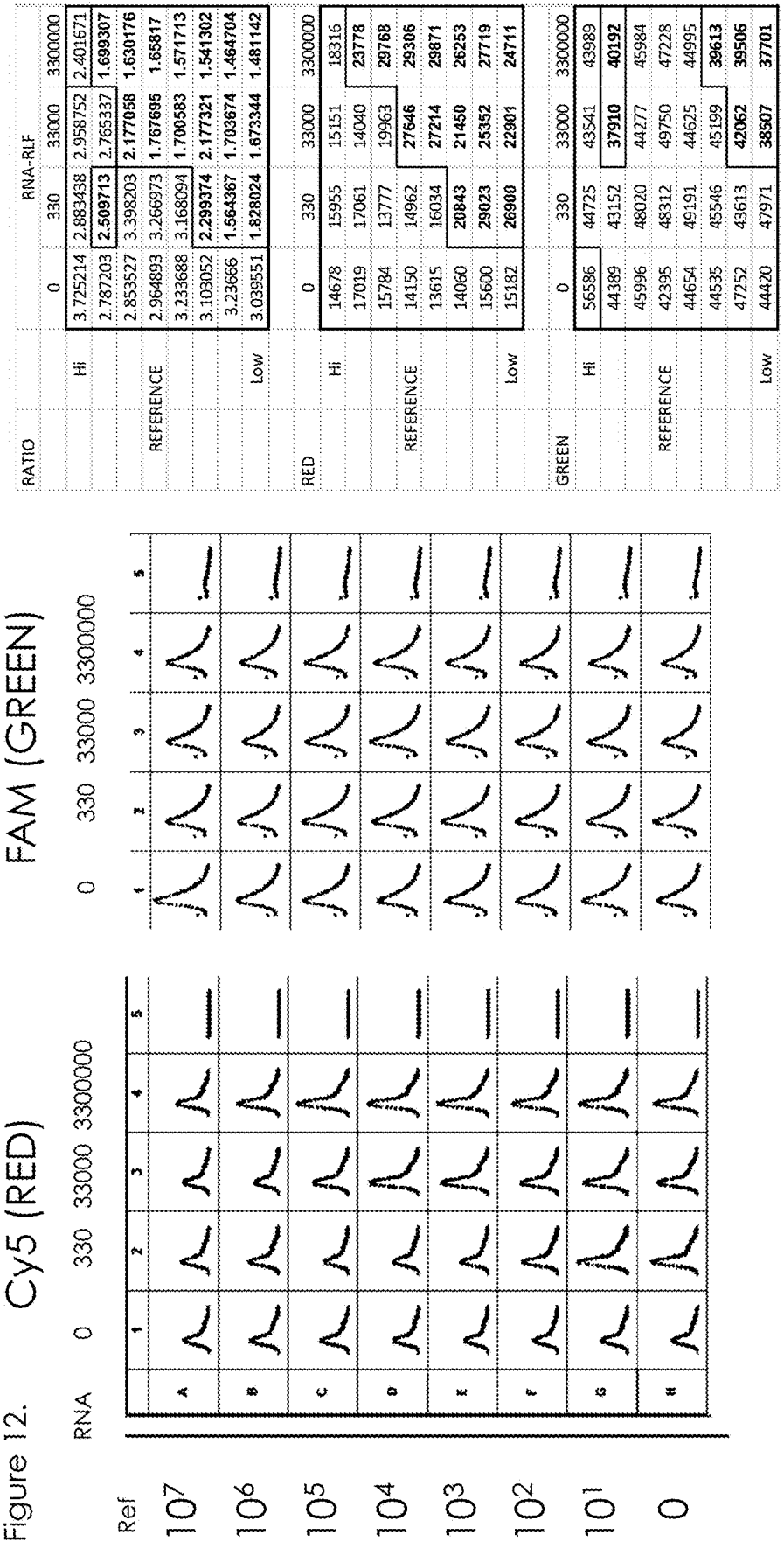
FIG. 12 shows microplate reader assessment of the competitive MTA example.

For this experiment, a 96-well plate was loaded with various combinations of reference nucleic acid and sample nucleic acid. Reference sequence concentrations spanned 0-10^7 copies of DNA per well (for a 10 microliter reaction). Sample sequence concentrations spanned 0-3.3*10^7 copies of RNA per well. LAMP reactions were performed according to standard practices with reverse transcriptase to facilitate RNA amplification. The results of the competitive seeding indicate successful digitization of the concentration signal. See FIG. 12. At left, the red fluorescence per well is indicated. Although each well seems to possess significant red fluorescence, where sample RNA concentrations overwhelm reference DNA the red fluorescence is markedly increased.

Likewise, in the green channel, significant signal exists in each well, but wells with less competition show an increase in the green signal. On the right FIG. 12, the fluorescence data is tabulated. The data at top shows the green to red fluorescence ratio. The middle table shows the red fluorescence signal. At bottom, the green fluorescence is shown for the various sample/reference combinations. From this data, it is apparent that the technique supports readout modalities that take account of both signals, or can be used single-ended by examining either the red or the green fluorescence.

FIG. 13 shows how green fluorescence (shown in 13a) vs. red fluorescence (shown in 13b) can be readily discerned by visual inspection. A cellular phone, in this case a Galaxy Note III, was affixed with a selectable filter set for red or green fluorescence. A hand-held flashlight with selectable color emission (blue emission for green excitation, and green emission for red fluorescence excitation) was used. The top image 13a shows a set of tubes illuminated for green fluorescence with the proper filter selected, as photographed using the same cellular phone. Green fluorescence is only observed in LAMP reactions that contained the FLF probe set. Likewise, the bottom image (13b) shows red fluorescence under proper illumination/filter combination, with red fluorescence only apparent in LAMP reactions that were supplemented with the RLF probe set. These images indicate that the probes are amenable to visual inspection, without the requirement of cameras or digitization elements. 13c shows a simple display device with a slots to display fluorescence.

These reactions were run with a quencher to fluorophore ratio of 30:1. In general, ratios of 1:1 to 30:1 are suitable for visualization. High quencher concentrations increase assay cost but improve background fluorescence levels. The optimum ratio will vary by particular probe pair and by the needs of the particular assay.

FIG. 14 illustrates that visualization of the threshold effect. In this case, as seen in 14a, the reaction tubes were placed on a fluorescence-imaging table. The table was only capable of measuring green fluorescence, but the digitization trend is nevertheless apparent, indicating the possibility of digitized assay with visual readout. Optimum formats include arrays of tubes, as shown in FIG. 14 or microfluidic devices as are known by those skilled in the art. 14*b* shows an example of green fluorescence. 14*c* shows an example of red fluorescence.

Figure 15:
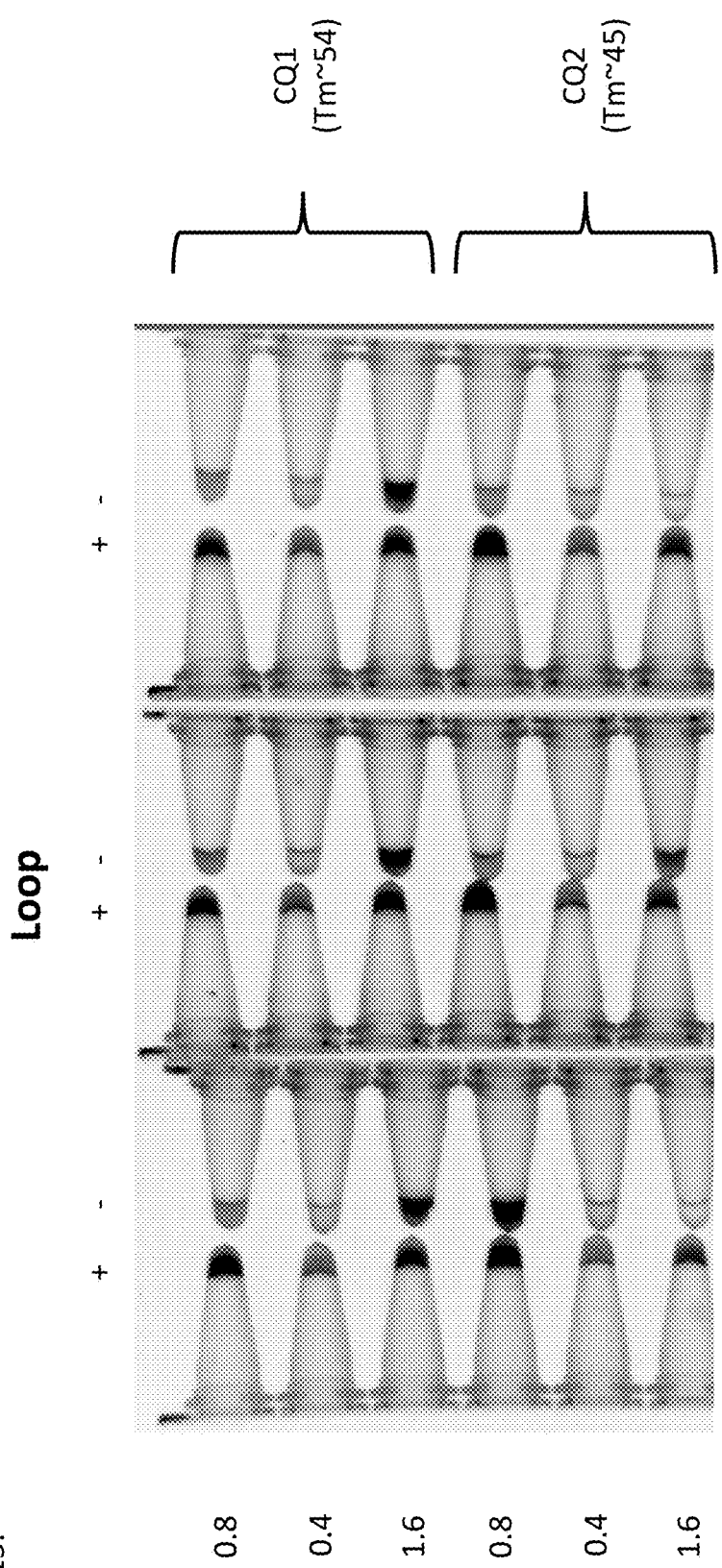
FIG. 15 shows example loop primers as probes.

FIG. 15 illustrates the efficacy of probe sets based on LF primers. Probes designed for one of two melting temperatures were tested (54 or 45 C) at various concentrations (0.4, 0.8, and 1.6 micromolar). At either temperature, 0.4 micromolar concentrations appear to be optimal. In particular, using 0.8 molar concentrations (which is commonly recommended Loop primer concentration), there is an apparent increase in false positives or poor contrast ratio.

Figure 16:
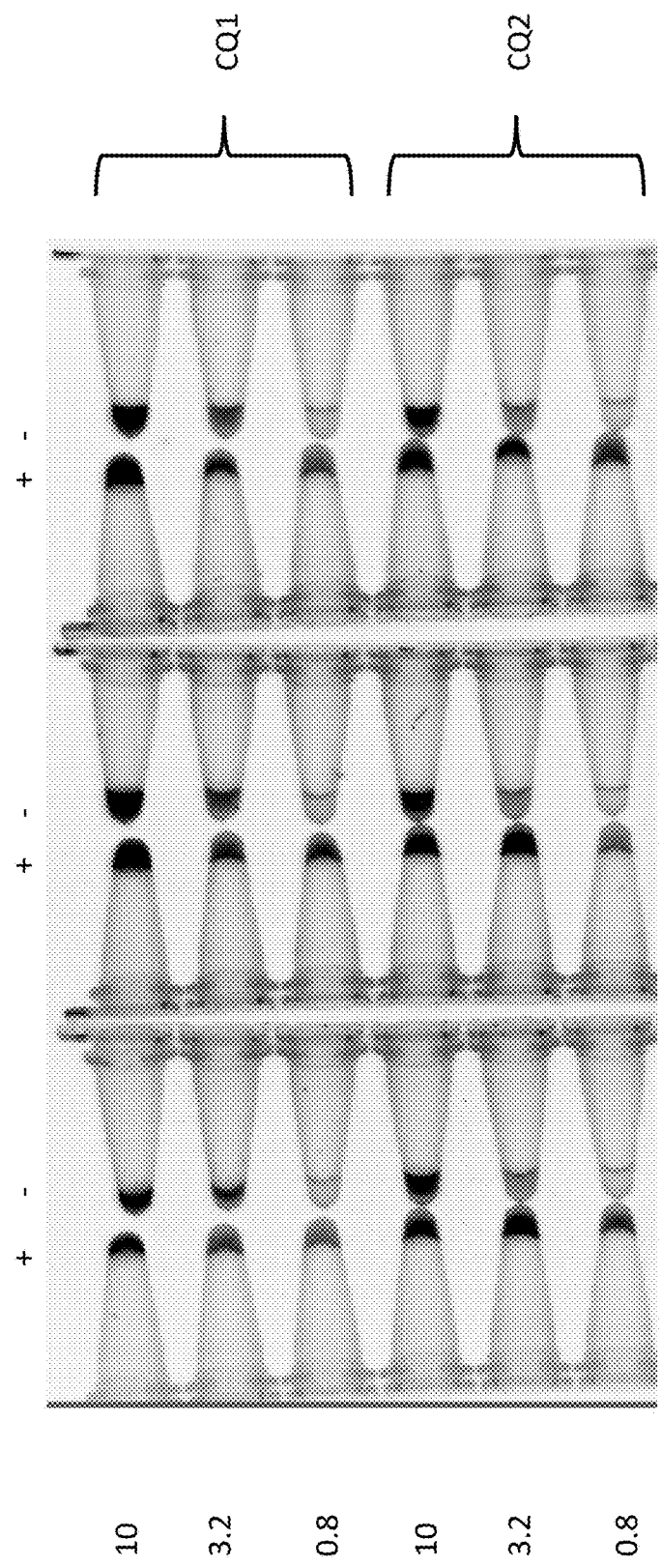
FIG. 16 shows example swarm primers as probes.

As mentioned above, other primers may be use as probes. FIG. 16 illustrates the results using swarm primers. Good specificity is seen up to 0.8 micromolar. This concentration is high enough to obtain most of the Swarm primer effect without incurring deleterious effects.

As noted above, other LAMP primers, such as stem primers, swarm primers, FIP and BIP may be used instead of loop primers. Generally, the specificity of a reaction is improved when assayed using quenching of unincorporated fluorophore-tagged primers. However, the degree of specificity increase still depends on the specific primer system.

Other alterations may be made without deviating from the scope of the invention. Accordingly, the system and method, the use, steps, order of steps, etc. may be varied as a matter of application specific design choice without deviating from the scope of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between.

We claim:

1. A method for conducting a quantitative end-point nucleic acid detection, said method comprising:
   providing a target sequence;
   providing a first primer comprising a secondary sequence;
   providing a second primer for amplification of the secondary sequence;
   synthesizing amplicons that incorporate the target sequence and the secondary sequence; and
   amplifying the secondary sequence via loop-mediated isothermal amplification (LAMP) to produce a visual signal.

2. The method of claim 1, wherein said method is performed in an isothermal condition.

3. The method of claim1, further comprising using an indicator dye.

4. The method of claim 1, wherein the first primer anneals to a forward primer 2c (F2c) region of the target sequence to initiate nucleic acid synthesis.

5. The method of claim 1, wherein said method is performed in a multi-well array.

6. The method of claim 5, wherein wells in the multi-well array comprise varying concentrations of the first primer and equal concentrations of the second primer.

7. The method of claim 5, further comprising analyzing and comparing visual signals from wells from the multi-well array.

8. A method for conducting a quantitative end-point nucleic acid detection via LAMP, said method comprising:
   providing a target sequence;
   providing a reference sequence comprising a tag region, wherein the reference sequence is identical to the target sequence but the tag region is in reverse orientation with respect to a corresponding region in the target sequence;
   providing a first primer which binds with the target sequence;
   providing a second primer which binds with the reference sequence; and
   conducting competitive reactions between the reference sequence and the target sequence.

9. The method of claim 8, wherein the tag region is located in a loop region.

10. The method of claim 8, wherein the first primer comprises a first visual indicator.

11. The method of claim 8, wherein the second primer comprises a second visual indicator.

12. The method of claim 9, wherein the first visual indicator is a fluorophore attached to the first primer.

13. The method of claim 9, wherein the second visual indicator is a fluorophore attached to the second primer.

14. The method of claim 8, wherein said method is performed in a multi-well array.

15. The method of claim 8, wherein the wells in the multi-well array comprise varying concentrations of the reference sequence and equal concentrations of the target sequence in each well.

16. The method of claim 8, further comprising analyzing and comparing visual signals from wells from the multi-well array.

17. The method of claim 8, further comprising a fluorophore-quencher pair, wherein such pair uses the first primer as an annealing template at room temperature.

18. The method of claim 8, further comprising a second fluorophore-quencher pair, wherein such pair uses the second primer as an annealing template at room temperature.

19. A method for producing a digital readout of nucleic acid detection, said method comprising:
   providing a sample target sequence;
   providing a reference sequence comprising a plurality of sequences identical to said target sequence and a tag region that is in reverse orientation with respect to a corresponding region in the target sequence;
   providing a first loop primer that binds with the sample target, said first loop primer having a first fluorescent molecule attached to its 5' end;
   providing a second loop primer that binds with the reference target, said second loop primer having a second fluorescent molecule attached to its 5' end;
   conducting competitive reactions using the sample target sequence and the reference sequence in a set of wells, wherein the concentration of the sample target sequence is equal across the wells and the the concentration of the reference sequence varies from across the wells; and
   analyzing the color and intensity of the fluorescence of the wells.

20. The method of claim 1, wherein the target sequence comprises a region of SEQ ID NO: 1.

* * * * *

SEQUENCE LISTING

```
<160> NUMBER OF SEQ ID NOS: 17

<210> SEQ ID NO 1
<211> LENGTH: 1500
<212> TYPE: DNA
<213> ORGANISM: human

<400> SEQUENCE: 1
atcaggtgca ttggagtcag caatagagac ttcgtggagg gcatgtcagg tgggacctgg    60
gttgatgttg tcttggaaca tggaggctgc gttaccgtga tggcacagga caagccaaca   120
gtcgacatag agttggtcac gacgacggtt agtaacatgg ccgaggtaag atcctattgc   180
tacgaggcat cgatatcgga catggcttcg gacagtcgtt gcccaacaca aggtgaagcc   240
taccttgaca agcaatcaga cactcaatat gtctgcaaaa gaacattagt ggacagaggt   300
tggggaaacg gttgtggact ttttggcaaa gggagcttgg tgacatgtgc caagtttacg   360
tgttctaaga agatgaccgg gaagagcatt caaccggaaa atctggagta tcggataatg   420
ctatcagtgc atggctccca gcatagcggg atgattggat atgaaactga cgaagataga   480
gcgaaagtcg aggttacgcc taattcacca agagcggaag caaccttggg aggctttgga   540
agcttaggac ttgactgtga accaaggaca ggccttgact tttcagatct gtattacctg   600
accatgaaca ataagcattg gttggtgcac aaagagtggt tcatgacat cccattgcct    660 tggcatgctg gggcagacac cggaactcca cactggaaca acaaagaggc attggtagaa   720
ttcaaggatg cccacgccaa gaggcaaacc gtcgtcgttc tggggagcca ggaaggagcc   780
gttcacacgg ctctcgctgg agctctagag gctgagatgg atggtgcaaa gggaaggctg   840
ttctctggcc atttgaaatg ccgcctaaaa atggacaagc ttagattgaa gggcgtgtca   900
tattccttgt gcactgcggc attcacattc accaaggtcc cagctgaaac actgcatgga   960
acagtcacag tggaggtgca gtatgcaggg acagatggac cctgcaagat cccagtccag  1020
atggcggtgg acatgcagac cctgacccca gttggaaggc tgataaccgc caacccgtg   1080 attactgaaa gcactgagaa ctcaaagatg atgttggagc ttgacccacc atttgggat   1140 tcttacattg tcataggagt tggggacaag aaaatcaccc accactggca taggagtggt  1200
agcaccatcg gaaaggcatt tgaggccact gtgagggcg ccaagagaat ggcagtcctg   1260
ggggatacag cctgggactt cggatcagtc gggggtgtgt tcaactcact gggtaagggc  1320
attcaccaga ttttggagc agccttcaaa tcactgtttg gaggaatgtc ctggttctca   1380
cagatcctca taggcacgct gctagtgtgg ttaggtttga acacaaagaa tggatctatc  1440
```
tccctcacat gcttggccct gggggagtg atgatcttcc tctccacggc tgtttctgct   1500

<210> SEQ ID NO 2
<211> LENGTH: 19
<212> TYPE: DNA
<213> ORGANISM: human

<400> SEQUENCE: 2
gggaaacggt tgtggactt                                                  19

<210> SEQ ID NO 3
<211> LENGTH: 19
<212> TYPE: DNA
<213> ORGANISM: human

<400> SEQUENCE: 3
gcttccgctc ttggtgaat                                                  19

<210> SEQ ID NO 4
<211> LENGTH: 40
<212> TYPE: DNA
<213> ORGANISM: human

<400> SEQUENCE: 4
ccggttgaat gctcttcccg ggcaaaggga gcttggtgac                           40

<210> SEQ ID NO 5
<211> LENGTH: 40
<212> TYPE: DNA
<213> ORGANISM: human

<400> SEQUENCE: 5
gctatcagtg catggctccc aggcgtaacc tcgactttcg                           40

<210> SEQ ID NO 6
<211> LENGTH: 19
<212> TYPE: DNA
<213> ORGANISM: human

<400> SEQUENCE: 6
gcaaagggag cttggtgac                                                  19

<210> SEQ ID NO 7
<211> LENGTH: 21
<212> TYPE: DNA
<213> ORGANISM: human

<400> SEQUENCE: 7
ccggttgaat gctcttcccg g                                               21

<210> SEQ ID NO 8
<211> LENGTH: 19
<212> TYPE: DNA
<213> ORGANISM: human

<400> SEQUENCE: 8
ggcgtaacct cgactttcg                                                  19

<210> SEQ ID NO 9
<211> LENGTH: 21
<212> TYPE: DNA
<213> ORGANISM: human

```
<400> SEQUENCE: 9
gctatcagtg catggctccc a                                          21

<210> SEQ ID NO 10
<211> LENGTH: 20
<212> TYPE: DNA
<213> ORGANISM: human

<400> SEQUENCE: 10
aacacgtaaa cttggcacat                                            20

<210> SEQ ID NO 11
<211> LENGTH: 21
<212> TYPE: DNA
<213> ORGANISM: human

<400> SEQUENCE: 11
agcgggatga ttggatatga a                                          21

<210> SEQ ID NO 12
<211> LENGTH: 300
<212> TYPE: DNA
<213> ORGANISM: human

<400> SEQUENCE: 12
actactacta ctgaattcaa ggataagcag ccaatgatca gggaaacggt tgtggacttt    60
ttggcaaagg gagcttggtg acatgtgcca agtttacgtg ttctaagaag atgaccggga   120
agagcattca accggaaaat ctggagtatc ggataatgct atcagtgcat ggctcccagc   180
atagcgggat gattggatat gaaactgacg aagatagagc gaaagtcgag gttacgccta   240
attcaccaag agcggaagca ctcctgctac ggaattcgga ataaacggc ccaaccctca   300

<210> SEQ ID NO 13
<211> LENGTH: 300
<212> TYPE: DNA
<213> ORGANISM: human

<400> SEQUENCE: 13
actactacta ctgaattcaa ggataagcag ccaatgatca gggaaacggt tgtggacttt    60
ttggcaaagg gagcttggtg acttgtgcat ttgaaccgtg tactaagaag atgaccggga   120
agagcattca accggaaaat ctggagtatc ggataatgct atcagtgcat ggctcccagc   180
atagcgggat gattggatat gaaactgacg aagatagagc gaaagtcgag gttacgccta   240
attcaccaag agcggaagca ctcctgctac ggaattcgga ataaacggc ccaaccctca   300

<210> SEQ ID NO 14
<211> LENGTH: 20
<212> TYPE: DNA
<213> ORGANISM: human

<400> SEQUENCE: 14
aacacgtaaa cttggcacat                                            20

<210> SEQ ID NO 15
<211> LENGTH: 13
<212> TYPE: DNA
<213> ORGANISM: human

<400> SEQUENCE: 15
ttgtgcattt acc                                                   13
```

```
<210> SEQ ID NO 16
<211> LENGTH: 20
<212> TYPE: DNA
<213> ORGANISM: human

<400> SEQUENCE: 16
tacacggttc aaatgcacaa                                                     20

<210> SEQ ID NO 17
<211> LENGTH: 13
<212> TYPE: DNA
<213> ORGANISM: human

<400> SEQUENCE: 17
atgtgccaat ccc                                                            13
```

UNITED STATES PATENT AND TRADEMARK OFFICE
CERTIFICATE OF CORRECTION

| | | |
|---|---|---|
| PATENT NO. | : 11,345,954 B2 | Page 1 of 1 |
| APPLICATION NO. | : 16/323393 | |
| DATED | : May 31, 2022 | |
| INVENTOR(S) | : Rhett Martineau and Deirdre Meldrum | |

It is certified that error appears in the above-identified patent and that said Letters Patent is hereby corrected as shown below:

In the Claims

Claim 3, Column 17, Line 36 reads:
"claim1"
Whereas it should read:
--claim 1--

Claim 19, Column 18, Line 58:
Delete the third occurrence of "the"

Claim 19, Column 18, Line 59 reads:
"sequence varies from across"
Whereas it should read:
--sequence varies across--

Signed and Sealed this
Third Day of January, 2023

Katherine Kelly Vidal
*Director of the United States Patent and Trademark Office*